United States Patent
Weiner et al.

(10) Patent No.: US 6,881,558 B1
(45) Date of Patent: Apr. 19, 2005

(54) EXPRESSION SYSTEM FOR CLONING TOXIC GENES

(75) Inventors: David B. Weiner, Merion Station, PA (US); Donghui Zhang, Philadelphia, PA (US); Adam Cohen, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 49 days.

(21) Appl. No.: 09/888,860

(22) Filed: Jun. 25, 2001

Related U.S. Application Data

(60) Provisional application No. 60/214,105, filed on Jun. 26, 2000.

(51) Int. Cl.⁷ .......................... C12P 21/06; C12P 21/04; C12N 1/12; C12N 15/00; C07H 21/04
(52) U.S. Cl. ................ 435/91.1; 435/252.1; 435/252.3; 435/320.1; 435/325; 435/348; 435/455; 435/69.1; 536/23.1; 536/24.1; 536/24.2
(58) Field of Search ............................... 435/69.1, 69.7, 435/69.8, 71.1, 172.1, 172.3, 252.1, 320.1, 325, 348, 456, 457; 536/231, 24.1, 24.2, 24.5

(56) References Cited

U.S. PATENT DOCUMENTS 5,385,839 A * 1/1995 Stinski .................. 435/366

OTHER PUBLICATIONS pBK–CMV information from Stratagene catalog.*
B Matthey et al., Gene, "A new series of pET–derived vectors for high efficiency expression of Pseudomonas exotoxin–bases fusion proteins," 1999, 229, pp. 145–153.*
MI Bukrinsky et al., Gene, "Multicopy expression vector based on temperature–regulated lac repressor:expression of human immunodeficiency virus env gene in *Escherichia coli*," 1988, 70, pp. 415–417.*
Expression Systems and Vectors, Invitrogen Catalog 1994, 5:41 & 66.*
Ratagene, Cloning Systems 1994, Creating the tools for the creative mind,pp. 18, 19 &45.*
Novagen, pET–27b(+) Vector, 1998, READSEQ Sequence Conversion Results, pp. 1–4.*

* cited by examiner

*Primary Examiner*—Gerry Leffers
*Assistant Examiner*—Maria Marvich
(74) *Attorney, Agent, or Firm*—Cozen O'Connor; Mark DeLuca; Paul K. Legaard

(57) ABSTRACT

Methods of cloning and/or amplifying toxic genes in bacteria using a vector which amplifies the toxic gene in bacteria and also allows subsequent expression in mammalian systems is provided. A vector having an origin of replication, a first promoter, a polylinker, a second promoter in reverse orientation with respect to the first promoter, a poly adenylation signal, and a gene encoding a selectable marker, and optionally an enhancer operably connected to the first promoter, and/or a nucleotide sequence encoding a toxic protein is also provided.

8 Claims, 3 Drawing Sheets

EXPRESSION SYSTEM FOR CLONING TOXIC GENES

CROSS-REFERENCE TO RELATED APPLICATIONS

This application claims priority to U.S. provisional application Ser. No. 60/214,105 filed Jun. 26, 2000, which is incorporated herein by reference in its entirety.

FIELD OF THE INVENTION

The present invention relates to vectors which suppress the expression of toxic genes, compositions comprising the same, and methods of using vectors to clone toxic genes in bacteria.

BACKGROUND OF THE INVENTION

Cloning of genes in bacterial systems has greatly expanded the scope of molecular biology and gene therapy. Many genes, however, have not yet been successfully cloned or sub-cloned by conventional cloning techniques due to their toxicity in host cells such as bacteria. For example, cloning and sub-cloning of env genes from HIV-1 has been particularly difficult due to the toxicity of env genes in bacteria. Neither directional cloning by two enzyme digestion nor unidirectional cloning by single enzyme digestion or blunt-end ligation has proven to be successful for env genes or portions thereof which are toxic in bacteria.

Several approaches have been examined for the ability to clone toxic genes in bacteria For example, using a cytomegalovirus promoter in bacteria has not been successful because the promoter is leaky and the resultant protein is toxic to the bacteria. A possible solution is to choose a promoter that is not leaky. However, due to the paucity of non-leaky promoters and promoters which are as strong as the cytomegalovirus promoter, this strategy has not proven to be very successful. Another possible solution is to choose a strain of bacteria that is not as vulnerable to the toxic gene. Several strains including DH5α, XL-1 Blue, Top10F', InvαF', Sure, and HB101 have been used without much success.

Another possible strategy for cloning toxic genes in bacteria is to use antisense technology to bind to the mRNA encoding the toxic gene. For example, bacteria could be co-transformed with two plasmids—one encoding the toxic gene and a second plasmid encoding the antisense strand, which is lost once the selective pressure, such as ampicillin, is removed. Results based on such a strategy, however, have not been successful possibly due to the incompatibility of the ori of the two plasmids or possible due to the harshness of the double selection of the competent cells. A disadvantage of this strategy is that two plasmids carrying a long identical insert would likely recombine.

Accordingly, there remains a need for cloning toxic genes in bacteria. The present invention provides a single plasmid that can be used to clone the toxic gene in bacteria yet allow expression in mammalian cells. The present invention also provides methods of cloning toxic genes in bacteria using the plasmids.

DESCRIPTION OF PREFERRED EMBODIMENTS

Figure 1:
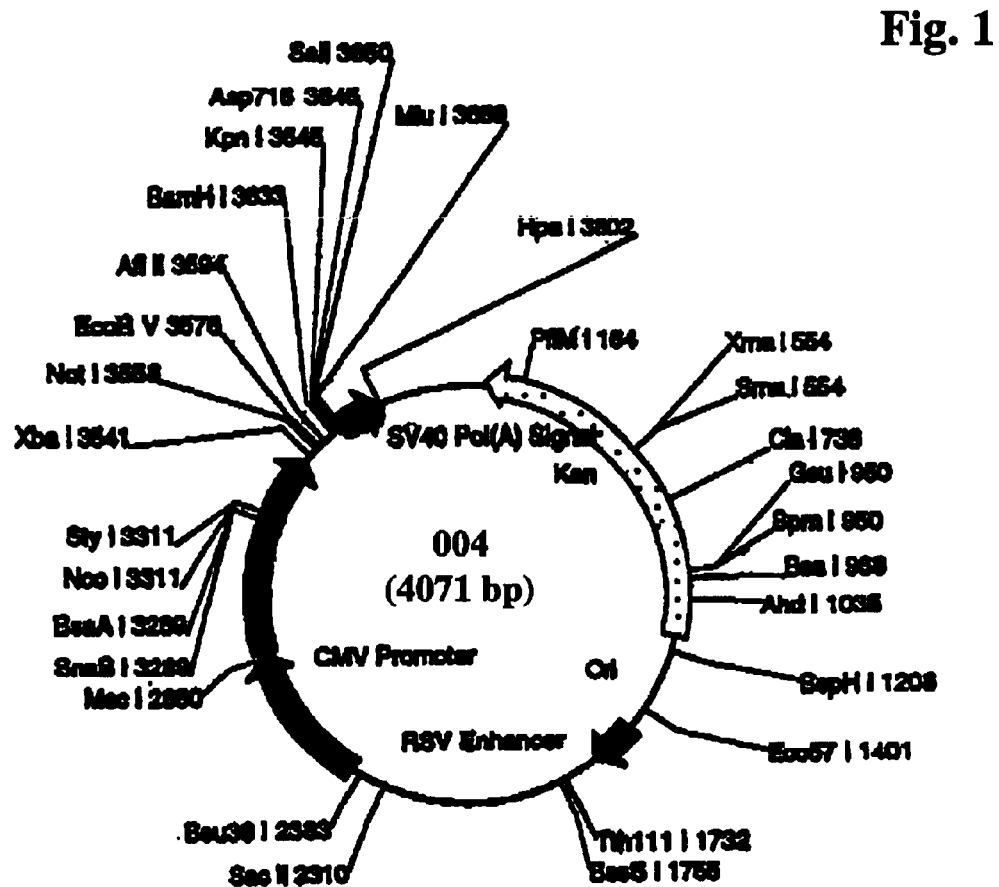
FIG. 1 represents a plasmid map of 004.

The present invention relates to methods of cloning toxic genes in bacteria using a vector which amplifies the toxic gene in bacteria and also allows subsequent expression in mammalian systems. The present invention also related to a host cell transformed with the plasmid of the invention.

The vectors of the invention are useful in, for example, general cloning of toxic genes, improving expression library cloning, and development of gene therapy products as part of or in association with a recombinant vaccine, attenuated vaccine or DNA vaccines. For library construction, the methods of the invention allow for the construction of complete libraries for mammalian expression by limiting toxic gene expression in bacterial systems. The present invention can also be used in vivo as components of a vaccine and as components of gene therapy using vectors.

The present invention is directed to a vector that can be used to clone one or more toxic genes in bacteria A preferred vector comprises an origin of replication, a first promoter, a polylinker, a second promoter in reverse orientation with respect to the first promoter, a poly A signal, and a gene encoding a selectable marker. The vector optionally comprises an enhancer operably connected to the first promoter. The vector can also comprise a nucleic acid molecule having a nucleotide sequence encoding a toxic protein.

The vectors of the invention include, but are not limited to, plasmids, cosmids, yeast artificial chromosomes, viral vectors, phagemids, and the like. The vector is preferably a plasmid. One skilled in the art is familiar with types of vectors that can be used in the present invention.

The vectors of the invention comprise an origin of replication. Functional origins of replication that can be used in the present invention include, but are not limited to, ColE1 origin of replication which allows replication in bacteria. One skilled in the art is readily familiar with origins of replication that can be used in the present invention.

The vectors of the invention also comprise a first promoter which directs the expression of the toxic gene, when present. The first promoter is either an inducible promoter or a constitutive promoter. Examples of first promoters that can be used in the present invention include, but are not limited to, cytomegalovirus promoters such as the CMV immediate early promoter, SV40 early promoter, mouse mammary tumor virus promoter, human immunodeficiency virus promoters such as the HIV long terminal repeat promoter, maloney virus promoter, Epstein Barr virus promoter, rous sarcoma virus promoter, ALV, B-cell specific promoters, baculovirus promoter for expression in insect cells, as well as promoters from human genes such as human actin, human myosin, human hemoglobin, human muscle creatine and human metalothionein. The first promoter is operably connected to the nucleic acid sequence encoding a toxic gene when the toxic gene is inserted into the vector.

The vectors of the invention also comprise a second promoter which is located downstream of the first promoter and is in reverse orientation relative to the first promoter. The second promoter is able to produce at least one antisense molecule directed to a nucleic acid molecule which is inserted upstream of the second promoter. The second promoter can be an inducible promoter or a constitutive promoter but must be specifically a bacterial promoter or a promoter active in bacteria. In addition, the second promoter must be inactive or silent in the target host, such as a human. Examples of second promoters that can be used in the present invention include, but are not limited to, a lac promoter. One skilled in the art is readily familiar with additional promoters that can be used in the present invention as a second promoter.

The vectors of the invention also comprise a polylinker or multiple cloning site which is located downstream of the first promoter and upstream of the second promoter (i.e., between the two promoters). The polylinker provides a site for insertion of the nucleic acid molecules encoding the toxic gene. Multiple cloning sites and polylinkers are well-known to those skilled in the art.

The vectors of the invention also comprise a polyadenylation signal. Examples of polyadenylation signals that can be used in the present invention include, but are not limited to, SV40 polyadenylation signal, human and bovine growth hormone polyadenylation signals, and LTR polyadenylation signals. In particular, the SV40 polyadenylation signal which is in pCEP4 plasmid (Invitrogen, San Diego Calif.), referred to as the SV40 polyadenylation signal, is used.

The vectors of the invention also preferably comprise a gene encoding a selectable marker in order to select for transformed bacteria. Examples of selectable markers that can be used in the present invention include, but are not limited to, kanamycin, neomycin, chloramphenicol, ampicillin, and genetic selection markers such as, for example, markers specific for tRNA selection.

The vectors of the invention can also optionally comprise an enhancer located upstream of the first promoter. Examples of enhancers that can be used in the present invention include, but are not limited to, rous sarcoma virus enhancer, human actin enhancer, human myosin enhancer, human hemoglobin enhancer, human muscle creatine enhancer, viral enhancers such as those from cytomegalovirus and Epstein-Barr virus, immunoglobulin enhancers, class II enhancers, and enhancers active in dendritic cells and macrophages. Enhancers and nucleic acid molecules comprising the same are widely known and available to those skilled in the art.

Other genetic elements are well known to those skilled in the art and can be used as deemed necessary. For example, the cis-acting transactivation element from Mason-Pfiz monkey virus can be used to facilitate transport of unspliced or partially spliced RNA to the cytoplasm. One skilled in the art is readily able to determine which additional genetic elements, if any, are required to express a particular toxic gene of interest.

The vectors described above can be used to clone toxic genes in bacteria A nucleic acid molecule having a nucleotide sequence that encodes a toxic gene is inserted into the multiple cloning site or polylinker of the vector. The nucleotide sequence is operably connected to the first promoter such that the toxic gene can be expressed in a host cell. The nucleotide sequence is also positioned such that the second promoter can direct the production of an antisense molecule in bacteria which targets the toxic gene RNA produced by the first promoter. In this manner, any RNA that is transcribed from the first promoter is physically bound by the antisense molecules produced by the second promoter, which prevents the RNA from being translated. Thus, no toxic protein is produced within the bacterial cell. Accordingly, the toxic gene can be cloned and amplified in bacteria without the problems associated with toxicity. Once the toxic genes are amplified in bacteria, the vectors comprising the toxic gene can be isolated and purified from the bacteria by standard procedures. The isolated vector can then be used to transfect mammalian cells wherein expression of the protein is desired. In target cells, since the second promoter is silent, no antisense RNA is produced and the sense RNA can be translated so as to express the desired protein in the target cell.

The toxic genes of the invention encode any toxic protein. The toxic genes can be complete genes or partial genes and preferably contain the necessary initiation signals and termination signals. Initiation codons and stop codon are generally considered to be part of the nucleotide sequence that encodes the desired toxic protein and are in frame with the coding sequence. The toxic genes can also be expressed as fusion proteins. Examples of toxic genes that can be used in the present invention include, but are not limited to, viral toxic genes, bacterial toxic genes, and fungal toxic genes. Preferred viral toxic genes include, but are not limited to, HIV-1 env gene. Preferred bacterial toxic genes include, but are not limited to, Pseudomonas exotoxin A, cholera toxin, diphtheria toxin, *E. coli* toxins, botulinum toxin, anthrax toxin, pertussis toxin, shiga toxin, ricin, tetanus toxin, Staphylococcal toxins, and the like. The nucleotide sequences of the toxins described above, as well as any others, can be found in numerous gene databases which are available to the public. Any toxic gene can be used in accordance with the present invention.

The present invention is also directed to a host cell comprising any of the vectors described above. The host cell can comprise a vector that does not contain a toxic gene or can comprise a vector that contains a toxic gene. The host, cell can be a bacterial cell including, but not limited to, DH5α, XL-1 Blue, Top10F', InvαF', Sure, Stb12, and HB101. The host cell can also be a mammalian cell including, but not limited to, non-human mammalian tissue culture cells, chinese hamster ovary cells, human tissue culture cells such as HeLa cells, and RD cells. Primate cells, including, but not limited to, COS cells, can also be used in the present invention.

One having ordinary skill in the art can use commercially available expression: vectors and systems or others to produce the vectors of the invention using routine techniques and readily available starting materials. (See e.g. Sambrook et al., *Molecular Cloning a Laboratory Manual,* Second Ed. Cold Spring Harbor Press (1989) which is incorporated herein by reference in its entirety.) A preferred starting vector is 004 (obtained from Apollon, Inc., Malvern, Pa.). However, additional commercially available vectors can also be used. pCDNA3 (Invitrogen) and pCITE (Novagen) can also be used. The vector can be digested with the appropriate restriction enzymes and the second promoter, such as the lac promoter, can be cloned into the cut site. The lac promoter can be obtained from, for example, pCRII (Invitrogen) or pUC18 and inserted in the reverse orientation into the starting vector and ligated The toxic gene of interest can then be inserted into the polylinker or multiple cloning site by standard techniques. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual,* Second Ed. Cold Spring Harbor Press (1989).

The present invention is also directed to a method of cloning a gene that is toxic, particularly to bacteria. A vector of the invention, such as any of the vectors described above containing the second promoter is reverse orientation, is provided. A nucleic acid molecule encoding a toxic gene of interest is inserted into the polylinker of the vector using routine procedures. Bacteria are transformed with the vector comprising the toxic gene, and the bacteria are grown under conditions in which the vector is amplified in the bacteria.

The vector can be isolated and purified from the bacteria by routine procedures and subsequently transfected into mammalian cells for expression, if desired.

The present invention also includes the addition of a marker protein for determining expression of a toxic protein in mammalian cells. The marker protein can be, for example, green fluorescent protein (GFP), which is ligated in frame with the first promoter such that expression of the toxic gene occurs along with expression of the toxic gene. In the case of GFP, the presence of the green fluorescence indicates that the toxic gene is produced. One skilled in the art can use a multitude of other markers, including fluorescent markers for the same purpose.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

Preparation of pDZ-1 and pDZ-1-GFP

Figure 2:
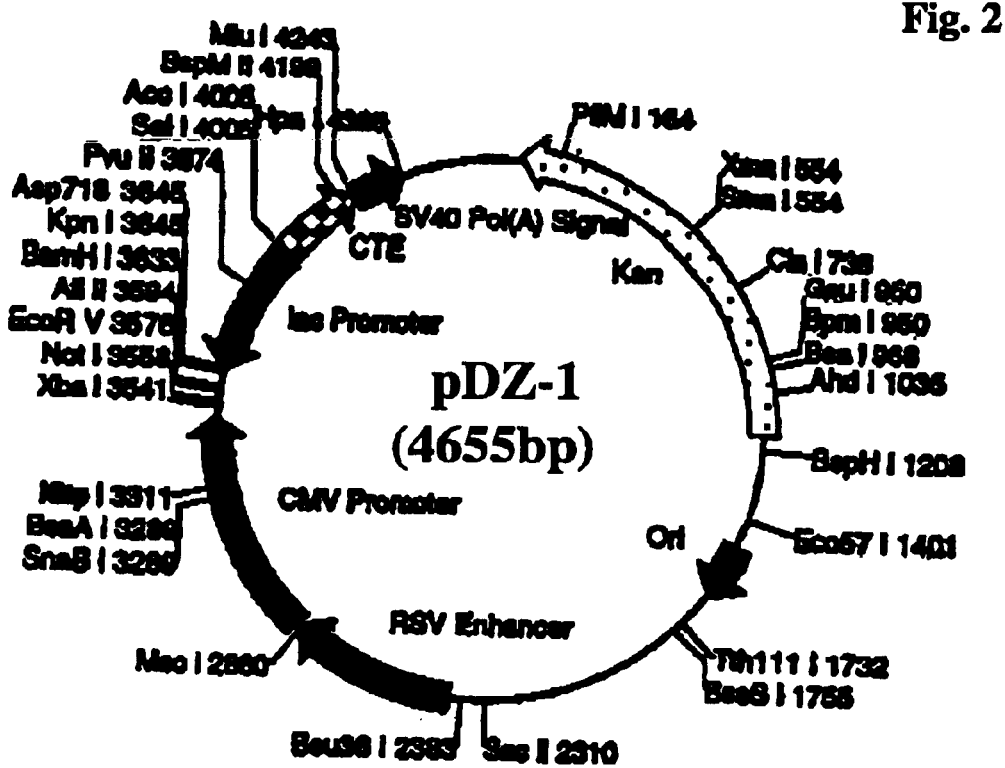
FIG. 2 represents a plasmid map of a preferred plasmid comprising a second promoter in reverse orientation relative to the first promoter.
Figure 3:
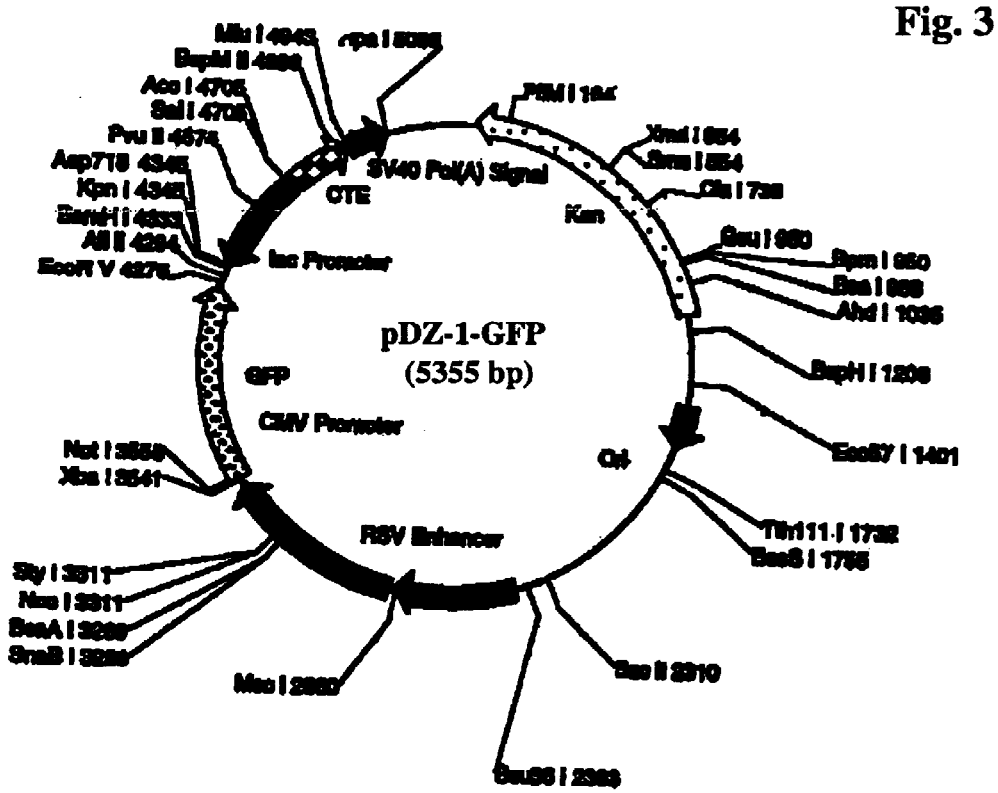
FIG. 3 represents a plasmid map of another preferred plasmid comprising a second promoter in reverse orientation and a green fluorescent protein operably connected to the first promoter.

The plasmid pDZ-1 was prepared by using plasmid 004 (see FIG. 1) as the starting vector. The lac promoter was obtained by PCR from the pCRII plasmid and digesting the PCR product with SalI and XbaI. Plasmid 004 was also digested with SalI and XbaI and the digested lac promoter PCR product was ligated into the plasmid to produce pDZ-1 (see FIG. 2). For pDZ-1-GFP (see FIG. 3), the green fluorescent protein was sub-cloned from pGreenLantern-1. Expression of pDZ-1-GFP was observed under ultraviolet light (not shown). Table 1 shows several HIV-1 env gene constructs that have been prepared in accordance with the claimed invention along with the percentage of positive clones.

TABLE 1

| Construct | Clade | % positive |
|---|---|---|
| 2424 | C | 10/18 |
| dj264 | A | 9/11 |
| 2430 | C | 15/16 |
| 2438 | A | 7/9 |
| 2425 | C | 15/18 |
| 2428 | E | 2/16 |
| 3095 | G | 2/2 |
| 3096 | G | 6/8 |
| 3112 | D | 7/8 |

What is claimed is:

1. A vector for amplifying a toxic gene in bacteria comprising:

an origin of replication;

a first promoter;

a polylinker;

a lac promoter in reverse orientation with respect to said first promoter;

a polyadenylation signal; and a nucleic acid molecule having a nucleotide sequence encoding a selectable marker;

wherein said lac promoter is capable of producing an antisense molecule directed to said toxic gene when a nucleotide sequence encoding a toxic gene product inserted into said polylinker of said vector.

2. A vector for amplifying a toxic gene in bacteria comprising:

an origin of replication;

a first promoter;

a polylinker;

a nucleic acid molecule having a nucleotide sequence encoding a toxic protein, wherein said nucleic acid molecule is inserted within said polylinker and is operably connected to said first promoter;

a second promoter in reverse orientation with respect to said first promoter;

a polyadenylation signal; and a nucleic acid molecule having a nucleotide sequence encoding a selectable marker;

wherein said second promoter is capable of producing an antisense molecule directed to said nucleic acid molecule encoding a toxic protein.

3. The vector of claim 2 wherein said nucleic acid molecule encoding a toxic protein encodes a bacterial toxin or a viral toxin.

4. The vector of claim 3 wherein said viral toxin is HIV-1 env.

5. The vector of claim 3 wherein said bacterial toxin is selected from the group consisting of Pseudomonas exotoxin A, cholera toxin, diphtheria toxin. *E. coli* toxins, botulinum toxin, anthrax toxin, pertussis toxin, shiga toxin, ricin, tetanus toxin, and Staphylococcal toxins.

6. A method of amplifying a toxic gene in bacteria comprising the steps;

providing a vector of claim 2;

inserting said vector comprising said toxic gene into said bacteria; and amplifying said vector in said bacteria.

7. A bacterial cell comprising the vector of claim 2.

8. A mammalian cell comprising the vector of claim 2.

* * * * *